(12) United States Patent
Puskas et al.

(10) Patent No.: US 10,314,945 B2
(45) Date of Patent: Jun. 11, 2019

(54) MODULAR SURFACE FUNCTIONALIZATION OF POLYISOBUTYLENE-BASED MATERIALS

(71) Applicants: Judit E. Puskas, Akron, OH (US); Alejandra Alvarez Albarran, Allison Park, PA (US); Emily Q. Rosenthal-Kim, Dublin, OH (US)

(72) Inventors: Judit E. Puskas, Akron, OH (US); Alejandra Alvarez Albarran, Allison Park, PA (US); Emily Q. Rosenthal-Kim, Dublin, OH (US)

(73) Assignee: THE UNIVERSITY OF AKRON, Akron, OH (US)

( * ) Notice: Subject to any disclaimer, the term of this patent is extended or adjusted under 35 U.S.C. 154(b) by 0 days.

(21) Appl. No.: 15/490,080

(22) Filed: Apr. 18, 2017

(65) Prior Publication Data

US 2017/0216492 A1 Aug. 3, 2017

Related U.S. Application Data

(63) Continuation of application No. 15/019,380, filed on Feb. 9, 2016, now abandoned.

(Continued)

(51) Int. Cl.
| | |
|---|---|
| *A61K 9/00* | (2006.01) |
| *A61L 27/48* | (2006.01) |
| *C08L 53/00* | (2006.01) |
| *C09D 153/00* | (2006.01) |
| *A61L 27/34* | (2006.01) |

(Continued)

(52) U.S. Cl.
CPC .............. *A61L 27/48* (2013.01); *A61L 27/34* (2013.01); *A61L 27/54* (2013.01); *A61L 29/085* (2013.01); *A61L 31/10* (2013.01); *B05D 1/02* (2013.01); *B05D 1/04* (2013.01); *C08F 8/14* (2013.01); *C08G 81/02* (2013.01); *C08J 7/047* (2013.01); *C08L 53/00* (2013.01); *C09D 153/00* (2013.01); *A61L 2300/606* (2013.01); *A61L 2420/02* (2013.01); *A61L 2420/04* (2013.01); *C08J 2323/22* (2013.01); *C08J 2423/26* (2013.01)

(58) Field of Classification Search
None
See application file for complete search history.

(56) References Cited

PUBLICATIONS

Alvarez et al; Modular Surface Functionalization of Polyisobutylene-Based Thermoplastic Elastomers; American Chemical Society meeting—Abstract publication; Oct. 9, 2013.

(Continued)

*Primary Examiner* — David Browe
(74) *Attorney, Agent, or Firm* — Renner Kenner Greive Bobak Taylor & Weber

(57) ABSTRACT

A polymer composite includes a functionalized polyisobutylene and an additional polyisobutylene-containing material. The functionalized polyisobutylene includes an α-lipoic acid functional group. A method for producing the polymer composite includes providing the additional polyisobutylene-containing material as a substrate having a surface, and coating the surface of the substrate with the functionalized polyisobutylene. A method for producing a coated substrate including the polymer composite includes providing a polymer combination including the functionalized polyisobutylene and the additional polyisobutylene-containing material, and depositing the polymer combination on to a substrate to thereby form the coated substrate.

19 Claims, 4 Drawing Sheets

Related U.S. Application Data

(60) Provisional application No. 62/113,621, filed on Feb. 9, 2015.

(51) Int. Cl.

| | |
|---|---|
| *A61L 31/10* | (2006.01) |
| *A61L 29/08* | (2006.01) |
| *C08J 7/04* | (2006.01) |
| *C08G 81/02* | (2006.01) |
| *C08F 8/14* | (2006.01) |
| *A61L 27/54* | (2006.01) |
| *B05D 1/02* | (2006.01) |
| *B05D 1/04* | (2006.01) |

(56) References Cited

PUBLICATIONS

Puskas et al.; Novel Thermoplastic Elastomers Based on Arborescent (Dendritic) Polyisobutylene with Short Copolymer End Sequences; Journal of Polymer Science: Part A, Polymer Chemistry; vol. 47, 1148-1158; 2009.

Foreman et al; Direct surface functionalization of novel biomaterials; American Chemical Society meeting—Abstract publication; Sep. 10, 2006.

MODULAR SURFACE FUNCTIONALIZATION OF POLYISOBUTYLENE-BASED MATERIALS

CROSS-REFERENCE TO RELATED APPLICATION

This application is a continuation of U.S. patent application Ser. No. 15/019,380, filed on Feb. 9, 2016, which claims priority to U.S. Provisional Patent Application No. 62/113,621 filed on Feb. 9, 2015; the contents of each are incorporated herein by reference.

STATEMENT REGARDING FEDERALLY SPONSORED RESEARCH OR DEVELOPMENT

This invention was made with government support under DMR 0509687 and DMR 0804878 awarded by the National Science Foundation. The government has certain rights in the invention.

FIELD OF THE INVENTION

The present invention generally relates to a polymer composite comprising a functionalized polyisobutylene and an additional polyisobutylene-containing material. The present invention further relates to one or more methods of making the polymer composite. The present invention further relates to one or more methods of surface modifying a polyisobutylene-containing material by attaching a functionalized polyisobutylene to a surface of the polyisobutylene-containing material.

BACKGROUND OF THE INVENTION

The increasing demand for new, specialized, biomaterials outpaces their development. One set of successful biomaterials includes those based on polyisobutylene (PIB). Polyisobutylene-containing thermoplastic elastomers, such as poly(styrene-b-isobutylene-b-styrene) (SIBS), have a wide variety of applications as biomaterials due to their unique, bioinert chemistry and broad range of tunable physical properties. One example of a PIB-based biomaterial is the Taxus® coronary stent developed by Boston Scientific, which features a SIBS coating. Its use over the past decade proves the biocompatibility and stability of SIBS in the human body. This long-term biostability is rare among polymers and demonstrates the unique properties of PIB-based polymers.

Certain compounds, such as poly(ethylene glycol), have been used to modify surfaces to improve their biocompatibility and to reduce protein adsorption. However, the surfaces that have been modified have primarily been hard surfaces, such as silicon wafers and gold chips.

There remains a need in the art to reduce protein adsorption for PIB-based polymers. Particularly, certain biomaterials, such as breast implants, are prone to failure by way of capsular contracture. It is believed that the fibrous capsule formation is initiated by the non-specific adsorption of proteins (i.e. fouling), specifically the protein fibrinogen (Fg). Thus, reducing adsorption of Fg will minimize fibrous capsule formation.

SUMMARY OF THE INVENTION

A first embodiment provides a polymer composite comprising a functionalized polyisobutylene and an additional polyisobutylene-containing material.

A second embodiment provides a polymer composite as in the first embodiment, wherein said functionalized polyisobutylene and said additional polyisobutylene-containing material are not attached by a covalent bond.

A third embodiment provides a polymer composite as in the either the first or second embodiment, wherein said additional polyisobutylene-containing material is non-functionalized.

A fourth embodiment provides a polymer composite as in any of the first through third embodiments, wherein said functionalized polyisobutylene includes a functional group selected from the group consisting of hydroxyl group, alkyl alcohols, ethylene glycol, oligomers of ethylene glycol, poly(ethylene glycol), poly(ethylene oxide), α-lipoic acid, amino acids, nucleic acids, saccharides, tocopherols, carotenoids, phosphatidylcholine, and combinations thereof.

A fifth embodiment provides a polymer composite as in any of the first through fourth embodiments, wherein the functional group includes a hydroxyl group.

A sixth embodiment provides a polymer composite as in any of the first through fifth embodiments, wherein the functional group includes α-lipoic acid.

A seventh embodiment provides a polymer composite as in any of the first through sixth embodiments, wherein said functionalized polyisobutylene further includes poly(ethylene glycol).

An eighth embodiment provides a polymer composite as in any of the first through seventh embodiments, wherein said additional polyisobutylene-containing material is selected from the group consisting of linear polyisobutylene TPEs, star polyisobutylene TPEs, and arborescent polyisobutylene TPEs.

A ninth embodiment provides a polymer composite as in any of the first through eighth embodiments, wherein said additional polyisobutylene-containing material is selected from the group consisting of linear poly(isobutylene(OH)-b-(isobutylene-co-para-methylstyrene)s, star poly(isobutylene(OH)-b-(isobutylene-co-para-methylstyrene)s, arborescent poly(isobutylene(OH)-b-(isobutylene-co-para-methylstyrene)s, linear poly(styrene-b-isobutylene-b-styrene)s, star poly(styrene-b-isobutylene-b-styrene)s, arborescent poly(styrene-b-isobutylene-b-styrene)s, linear poly(isobutylene-OH-co-para-methylstyrene), star poly(isobutylene-OH-co-para-methylstyrene), arborescent poly(isobutylene-OH-co-para-methylstyrene), linear poly(alloocimene-b-isobutylene-b-alloocimene), star poly(alloocimene-b-isobutylene-b-alloocimene), and arborescent poly(alloocimene-b-isobutylene-b-alloocimene).

A tenth embodiment provides a polymer composite as in any of the first through ninth embodiments, the composite being coated on a substrate.

An eleventh embodiment provides a polymer composite as in any of the first through tenth embodiments, wherein said substrate is selected from the group consisting of a breast implant, a stent, a knee implant, a catheter, and a wire.

A twelfth embodiment provides a polymer composite as in any of the first through eleventh embodiments, wherein said substrate is a biocompatible material.

A thirteenth embodiment provides a polymer composite as in any of the first through twelfth embodiments, wherein the composite has a protein adsorption of less than 50 ng/cm$^2$ with respect to the protein fibrinogen.

A fourteenth embodiment provides a polymer composite as in any of the first through thirteenth embodiments, wherein the composite includes a drug or molecule attached to the surface.

A fifteenth embodiment provides a method for producing the polymer composite as in any of the first through fourteenth embodiments, where the additional polyisobutylene-containing material is a substrate having a surface, the method comprising the step of coating the surface of the substrate with the functionalized polyisobutylene.

A sixteenth embodiment provides a method as in the fifteenth embodiment, where the step of coating includes spray coating the functionalized polyisobutylene on to the surface of the substrate.

A seventeenth embodiment provides a method as in the fifteenth embodiment, where the step of coating includes dipping the surface of the substrate in a solution containing the functionalized polyisobutylene.

An eighteenth embodiment provides a method for producing the polymer composite as in any of the first through fourteenth embodiments, comprising the steps of providing a polymer combination comprising the functionalized polyisobutylene and the additional polyisobutylene-containing material, and depositing the polymer combination on to a substrate.

A nineteenth embodiment provides a method as in the eighteenth embodiment, where the step of depositing is electrospraying.

A twentieth embodiment provides a method as in the eighteenth embodiment, where the step of depositing is electrospinning.

BRIEF DESCRIPTION OF THE DRAWINGS

Advantages of the present invention will become better understood with regard to the following description, appended claims, and accompanying drawings wherein:

DETAILED DESCRIPTION OF ILLUSTRATIVE EMBODIMENTS

Figure 1:
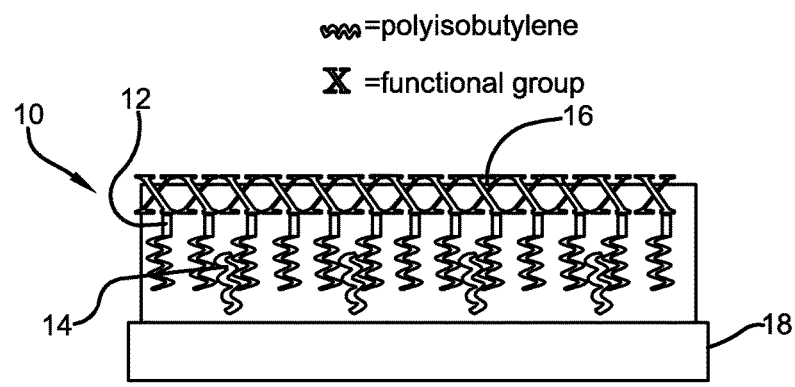
FIG. 1 is a schematic representation of a polymer composite of the present invention.
Figure 2:
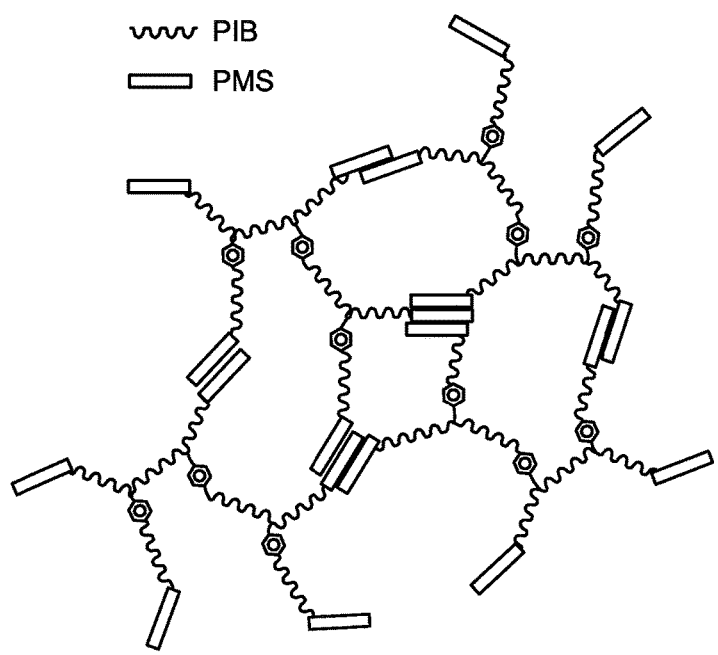
FIG. 2 is a schematic representation of an arborescent polyisobutylene-containing material with poly(para-methylstyrene) (PMS) end blocks (arbPIB-MS).

With reference to FIG. 1, a polymer composite 10 includes a functionalized polyisobutylene compound 12 and additional polyisobutylene 14. Additional polyisobutylene 14 may also be described as polyisobutylene-containing material 14. Polymer composite 10 includes an outer surface 16 and the functional group ends of the functionalized polyisobutylene compounds 12 tend to migrate to outer surface 16. In one or more embodiments, the functional group ends of the functionalized polyisobutylene compounds 12 are located at outer surface 16. In one or more embodiments, polymer composite 10 is applied to a substrate 18. As will be described further below, either functionalized polyisobutylene compound 12 can be applied to a substrate containing additional polyisobutylene 14, or functionalized polyisobutylene compound 12 can be pre-mixed with additional polyisobutylene 14 and then applied to a substrate.

Polyisobutylene-containing material 14, which may also be referred to as polyisobutylene-containing polymer 14 or additional polyisobutylene 14, contains polyisobutylene (PIB) polymer. By "additional," it is meant that polyisobutylene-containing material 14 is provided in addition to functionalized polyisobutylene compound 12. Polyisobutylene-containing material 14 may also be referred to as base polymer 14 or substrate 14. In one or more embodiments, polyisobutylene-containing material 14 is simply polyisobutylene polymer. In other embodiments, polyisobutylene-containing material 14 is selected from the group consisting of co-polymers and thermoplastic elastomers (TPE) that contain polyisobutylene polymer.

In one or more embodiments, polyisobutylene-containing material 14 may be an arborescent material. For purposes of this specification, arborescent may also be described as hyperbranched or dendritic. In one or more embodiments, polyisobutylene-containing material 14 is an arborescent PIB-based TPE with poly(para-methylstyrene) end blocks (arbPIB-MS).

In embodiments where functionalized polyisobutylene compound 12 is applied to polyisobutylene-containing material 14, the polyisobutylene-containing material 14 may be described as a bulk polymer. By bulk polymer, it is meant that the surface of the polyisobutylene-containing material 14 is being modified by the functionalized polyisobutylene compound 12. Bulk polymer may also refer to a polymer that has a molecular weight greater than its entanglement molecular weigh.

In one or more embodiments, polyisobutylene-containing material 14 is selected from the group consisting of linear polyisobutylene TPEs, star polyisobutylene TPEs, arborescent polyisobutylene TPEs, linear poly(isobutylene(OH)-b-(isobutylene-co-para-methylstyrene)s, star poly(isobutylene(OH)-b-(isobutylene-co-para-methylstyrene)s, arborescent poly(isobutylene(OH)-b-(isobutylene-co-para-methylstyrene)s, linear poly(styrene-b-isobutylene-b-styrene)s, star poly(styrene-b-isobutylene-b-styrene)s, arborescent poly(styrene-b-isobutylene-b-styrene)s, linear poly(isobutylene-OH-co-para-methylstyrene), star poly(isobutylene-OH-co-para-methylstyrene), arborescent poly(isobutylene-OH-co-para-methylstyrene), linear poly(alloocimene-b-isobutylene-b-alloocimene), star poly(alloocimene-b-isobutylene-b-alloocimene), arborescent poly(alloocimene-b-isobutylene-b-alloocimene).

Polyisobutylene-containing material 14 can be characterized by number average molar mass ($M_n$). In one or more embodiments, the number average molar mass of polyisobutylene-containing material 14 is from 5,000 to 500,000, in other embodiments from 10,000 to 400,000, and in other embodiments, from 50,000 to 300,000. In one or more embodiments, the number average molar mass of polyisobutylene-containing material 14 is from 100,000 to 300,000, and in other embodiments, from 150,000 to 250,000. In one or more embodiments, the number average molar mass of polyisobutylene-containing material 14 is 210,000 g/mol or approximate thereto. In one or more embodiments, the number average molar mass of polyisobutylene-containing material 14 is 200,000 g/mol or approximate thereto.

Polyisobutylene-containing material 14 can be characterized by polydispersity index ($M_w/M_n$). In one or more embodiments, the polydispersity index of polyisobutylene-containing material 14 is less than 5.0, in other embodiments less than 3.5, and in other embodiments less than 3.0. In one or more embodiments, the polydispersity index of polyisobutylene-containing material 14 is less than 2.5, and in other embodiments less than 2.0. In one or more embodiments, the polydispersity index of polyisobutylene-containing material 14 is 1.7 or approximate thereto. In one or more embodiments, the polydispersity index of polyisobutylene-containing material 14 is 2.8 or approximate thereto.

Polyisobutylene-containing material 14 can be characterized by wt. % para-methylstyrene. In one or more embodiments, the para-methylstyrene of polyisobutylene-containing material 14 is from 1% to 40%, in other embodiments from 3% to 25%, and in other embodiments from 3% to 15%. In one or more embodiments, the wt. % para-methylstyrene of polyisobutylene-containing material 14 is 3.5% or approximate thereto. In one or more embodiments, the wt. % para-methylstyrene of polyisobutylene-containing material 14 is 13% or approximate thereto. In one or more embodiments, the wt. % para-methylstyrene of polyisobutylene-containing material 14 is more than 3%. In one or more embodiments, the wt. % para-methylstyrene of polyisobutylene-containing material 14 is less than 15%.

Functionalized polyisobutylene compound 12 includes polyisobutylene and a functional group. The functionalized polyisobutylene compound 12 should be chemically compatible with polyisobutylene-containing material 14. For example, functionalized polyisobutylene compound 12 and polyisobutylene-containing material 14 might be chemically compatible simply because they both contain polyisobutylene.

In one or more embodiments, functionalized polyisobutylene compound 12 contains a PIB-containing polymer and a functional group chemically bonded to the PIB-containing polymer. The functional group is a chemical configuration not intrinsic to PIB-containing polymers. The functional group may also be described as a moiety or residue. Functionalized polyisobutylene compound 12 may be represented as PIB-X, where X represents a functional group.

The functional group is provided to impart a surface characteristic disparate from the bulk polymer, or to facilitate further chemistry, or to impart a surface characteristic disparate from the bulk polymer and facilitate further chemistry. An example of a surface characteristic is a thymine functional group imparting the ability for hydrogen bonding at the surface, which permits for the attachment of drugs or other molecules to the surface. An example of facilitating further chemistry is when the functional group enables the addition of a disparate chemical group. Certain functional groups are able to fulfill both purposes as they both change the surface properties and facilitate further chemistry.

In one or more embodiments, the functional group is selected from the group consisting of a hydroxyl group, alkyl alcohols, ethylene glycol, oligomers of ethylene glycol, poly(ethylene glycol), poly(ethylene oxide), α-lipoic acid, amino acids, nucleic acids, saccharides, tocopherols, carotenoids, phosphatidylcholine, and combinations thereof. Exemplary oligomers of ethylene glycol include tetraethylene glycol and hexaethylene glycol. Where functionalized polyisobutylene compound 12 includes a combination of functional groups, the combination may be either a chemical combination or a physical combination. Where a hydroxyl group is utilized as a functional group, the functional group can provide one or more of the following surface characteristics: the ability to hydrogen bond, increased hydrophilicity, and reduced protein fouling.

In one or more embodiments, functionalized polyisobutylene compound 12 can be provided in solution with a solvent. The solvent can be selected from the group consisting of hexane, toluene, methylcyclohexane, tetrahydrofurane, and dichloromethane.

In embodiments where functionalized polyisobutylene compound 12 is applied to polyisobutylene-containing material 14, it can be said that the method of applying functionalized polyisobutylene compound 12 is a modular method. Similarly, in these embodiments, polymer composite 10 might be described as a modular composite. By modular, it is meant that layers can be added. In one or more embodiments polymer composite 10 includes a plurality of layers of functionalized polyisobutylene compound 12. These layers may be similar or different. In one or more embodiments, polymer composite 10 include a functionalized polyisobutylene compound 12 layer and one or more other polymer layers. The modular nature allows for incorporating changes into one layer without altering the properties of the other layers.

In embodiments where functionalized polyisobutylene compound 12 is applied to polyisobutylene-containing material 14, it should be appreciated that the attachment, or "gluing," of the functionalized polyisobutylene compound 12 with the polyisobutylene-containing material 14 is not a covalent bond. To say further, the present invention is distinguished from the mere attachment of a functional group to a surface by way of a covalent bond. Indeed, applying functionalized polyisobutylene compound 12 to polyisobutylene-containing material 14 can be a simpler method than covalently bonding a functional group to a surface.

In these embodiments where functionalized polyisobutylene compound 12 is applied to polyisobutylene-containing material 14, the polyisobutylene-containing material 14, or bulk polymer 14, is covered by a layer of functionalized polyisobutylene compound 12. In one or more embodiments, the thickness of bulk polymer 14 is from 1 nm to 1 mm, in other embodiments from 10 nm to 100 micron, and in other embodiments from 20 nm to 50 micron. In one or more embodiments, the thickness of bulk polymer 14 is from 1 nm to 1 micron, in other embodiments from 50 micron to 100 micron, and in other embodiments from 100 micron to 1 mm. In one or more embodiments, the thickness of bulk polymer 14 is less than 1 micron. In one or more embodiments, the thickness of bulk polymer 14 is less than 20 nm. In one or more embodiments, the thickness of a functionalized polyisobutylene compound 12 layer is from 1 nm to 1 mm, in other embodiments from 10 nm to 100 micron, and in other embodiments from 20 nm to 50 micron. In one or more embodiments, the thickness of a functionalized polyisobutylene compound 12 layer is from 1 nm to 1 micron, in other embodiments from 50 micron to 100 micron, and in other embodiments from 100 micron to 1 mm. In one or more embodiments, the thickness of a functionalized polyisobutylene compound 12 layer is less than 1 micron. In one or more embodiments, the thickness of a functionalized polyisobutylene compound 12 layer is less than 20 nm.

Because the functionalized polyisobutylene compound 12 and polyisobutylene-containing material 14 are chemically compatible, the polymer chains of each layer entangle with the other layer during the application process. Thus, during this process, the two layers, or multiple layers, combine to form a single polymer article layer. It is believed that the outer layer, or surface layer, of polyisobutylene-containing material 14 softens, which allows the PIB block of the functionalized polyisobutylene compound 12 to penetrate and entangle into the surface layer of the polyisobutylene-containing material 14.

Also, during the layering process, the polymer chains have sufficient mobility as to allow the functional groups of the functionalized polyisobutylene compound 12 to migrate to the surface. This changes the chemistry of the surface. The functional groups migrate to and concentrate at the surface because they are chemically dissimilar from the bulk polymer. They migrate to the surface in order to minimize free energy.

Figure 3:
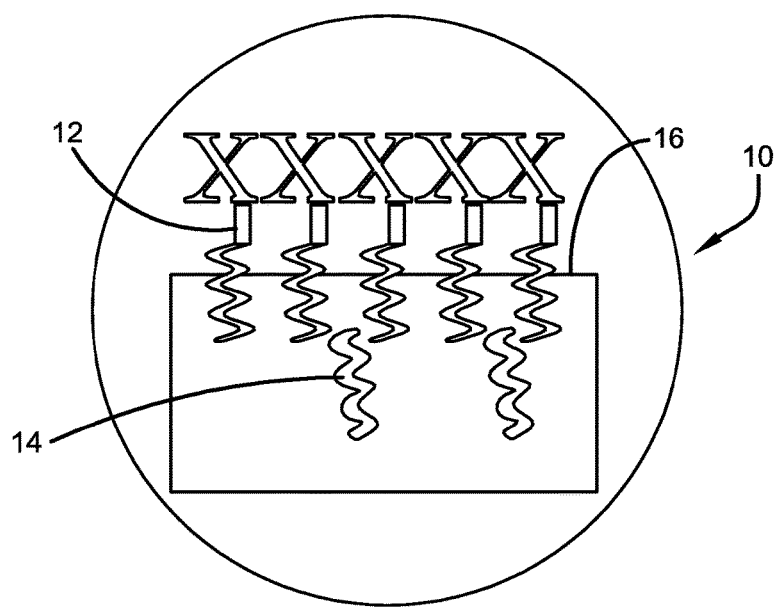
FIG. 3 is a schematic representation of a polymer composite of the present invention upon immersion in an aqueous solution.

In addition to the functional groups migrating to the surface in embodiments where a layering process is used, functional groups can also migrate to the surface in embodiments where functionalized polyisobutylene compound 12 and polyisobutylene-containing material 14 are pre-mixed. The functional groups near the surface move, or reorient, depending on the substance in contact with the surface. For example, hydrophilic functional groups move, or reorient, more to the surface when the surface is exposed to water than when it is exposed to air. Functional groups that are polar groups will also further migrate to the surface when the surface is immersed in water, an aqueous solution, or simulated body fluid. FIG. 3 shows a schematic representation of the functional groups further migrating to the surface when immersed in water. This further migration causes reduced protein adsorption.

In one or more embodiments, polymer composite 10 is on a substrate 18. Substrate 18 can also be described as coated substrate 18. In one or more embodiments, polymer composite 10 serves to increase to biocompatibility of substrate 18. In one or more embodiments, substrate 18 is a biocompatible material.

In one or more embodiments, the thickness of polymer composite 10 is from 1 nm to 1 mm, in other embodiments from 10 nm to 100 micron, and in other embodiments from 20 nm to 50 micron. In one or more embodiments, the thickness of polymer composite 10 is from 1 nm to 1 micron, in other embodiments from 50 micron to 100 micron, and in other embodiments from 100 micron to 1 mm. In one or more embodiments, the thickness of polymer composite 10 is less than 1 micron. In one or more embodiments, the thickness of polymer composite 10 is less than 20 nm.

It is believed that polymer composite 10 will serve to reduce the protein adsorption to substrate 18, particularly Fg adsorption. For example, where substrate 18 is a breast implant, polymer composite 10 reduces the Fg adsorption on the implant, thereby reducing fibrous capsule formation on the implant.

In addition to a breast implant, exemplary substrates 18 include other biomedical applications, such as stents, knee implants, and catheters. In one or more embodiments, substrate 18 is a wire and polymer composite 10 serves as a wire coating. In other embodiments, polymer composite 10 may serve to provide a non-fouling coating to a substrate 18, such as on a ship hull to prevent barnacle adhesion. Other suitable applications may be known to those skilled in the art.

In one or more embodiments, polymer composite 10 includes a filler material. In one or more embodiments, the filler material is in polyisobutylene-containing material 14. Exemplary filler materials include carbon black, silica, clay, and starch. In one or more embodiments, a filler is present in polymer composite 10 in an amount from 1 to 50 parts by weight for every 100 parts by weight of polymer composite 10, and in other embodiments from 5 to 40 parts by weight for every 100 parts by weight of polymer composite 10. In one or more embodiments, a filler is present in polyisobutylene-containing material 14 in an amount from 1 to 50 parts by weight for every 100 parts by weight of polyisobutylene-containing material 14, and in other embodiments from 5 to 40 parts by weight for every 100 parts by weight of polyisobutylene-containing material 14.

As discussed herein, polymer composite 10 reduces the protein adsorption to substrate 18. As well known in the art, proteins are biomolecules that are composed of amino acid subunits. Protein adsorption occurs when proteins accumulate at and adhere to a surface, but do not fully penetrate the substrate. When a non-native material enters the body, the first step of the immune response takes place and proteins in the body aggregate to the material in attempts to contain, neutralize, or wall-off the non-native material. This protein aggregation and adsorption is believed to be the cause of biomaterial fouling.

The migration of the functional groups to the surface 16 aids in preventing protein adsorption, particularly when polymer composite is present in a body or a simulated bodily fluid. The first step of inflammatory response is protein adsorption, so preventing protein adsorption is desired.

Polymer composite 10 can be characterized by the adsorption of the protein fibrinogen. As used herein, protein adsorption is measured using the outermost layer, which is generally in contact with the body or other protein source. In one or more embodiments, the adsorption of fibrinogen is less than 100 $ng/cm^2$, in other embodiments less than 50 $ng/cm^2$, and in other embodiments less than 25 $ng/cm^2$. In one or more embodiments, the adsorption of fibrinogen to a layer containing PEG-OCH$_3$ is less than 50 $ng/cm^2$. In one or more embodiments, the adsorption of fibrinogen to a layer containing PEG-OH is less than 25 $ng/cm^2$. In one or more embodiments, the adsorption of fibrinogen to a layer containing lipoic acid ester is less than 14 $ng/cm^2$.

In one or more embodiments, the water contact angle of a polymer composite 10 is from 70 to 170. In one or more embodiments, the water contact angle of a polymer composite 10 is from 80 to 150. In one or more embodiments, the water contact angle of a polymer composite 10 is from 90 to 130.

The present invention also provides one or more methods of making a polymer composite 10. As suggested above, either functionalized polyisobutylene compound 12 can be applied to a substrate containing additional polyisobutylene 14, or functionalized polyisobutylene compound 12 can be pre-mixed with additional polyisobutylene 14 and then applied to a substrate. Applying functionalized polyisobutylene compound 12 to a substrate containing additional polyisobutylene 14 can be done by methods known in the art. Exemplary methods include spraying, spin coating, and dipping. Pre-mixing functionalized polyisobutylene compound 12 with additional polyisobutylene 14 can also be done by methods known in the art. Exemplary methods include electrospraying and electrospinning.

Figure 5:
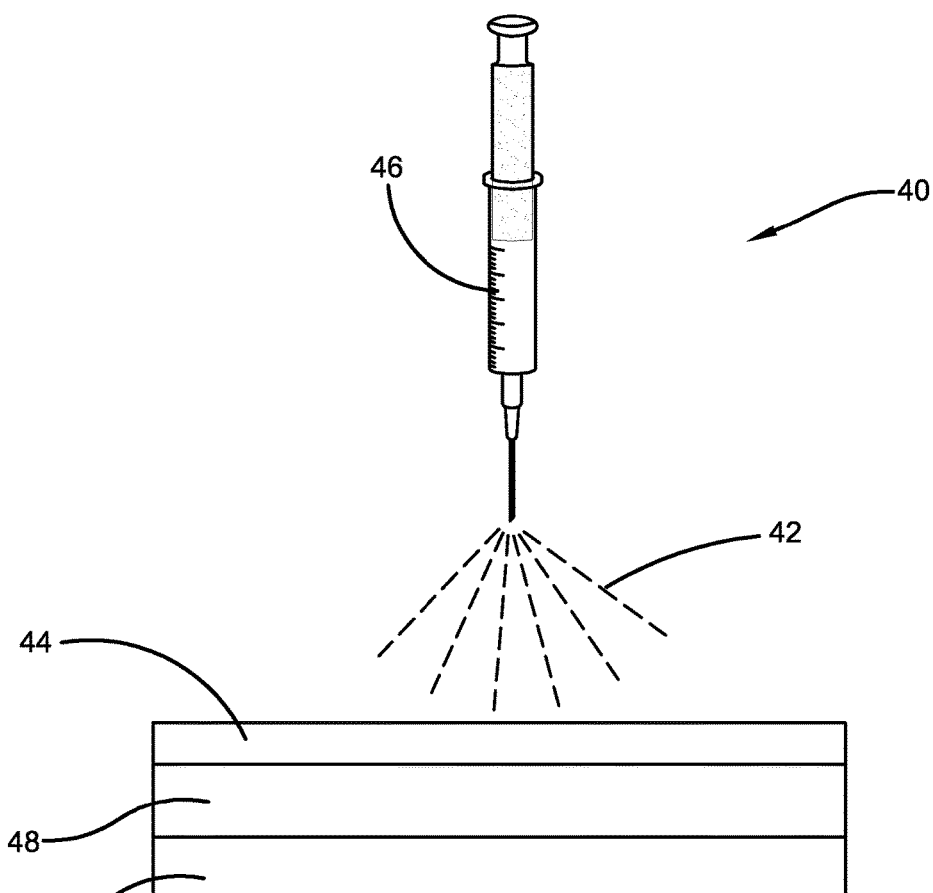
FIG. 5 is a schematic representation of a spin coating apparatus.

A schematic of a spin coating apparatus 40 is shown in FIG. 5. In general, spin coating is a procedure used to deposit uniform thin films to flat substrates. Usually a small amount of coating material is applied on the center of the substrate, which is either spinning at low speed or not spinning at all. The substrate is then rotated at high speed in order to spread the coating material by centrifugal force. A machine used for spin coating is called a spin coater, or simply spinner.

With reference to FIG. 5, functionalized polyisobutylene compound 42 is applied to additional polyisobutylene 44 by a depositing device 46, such as a syringe. Additional polyisobutylene 44 is positioned on a substrate 48, which is positioned on a spinner 50. The spinner 50 and substrate 48 are rotated at high speed in order to spread the functionalized polyisobutylene compound 42 on additional polyisobutylene 44 by centrifugal force. Functionalized polyisobutylene compound 42 can be selected from those materials described above for functionalized polyisobutylene compound 12. Additional polyisobutylene 44 can be selected from those materials described above for additional polyisobutylene 14. Substrate 48 can be selected from those materials described above for substrate 18.

One or more aspects of a spin coating process may be disclosed in U.S. Pat. Nos. 4,899,688 and 8,042,486, which are incorporated herein by reference.

In general, a dipping procedure includes immersing a substrate into a container having coating material, removing the piece from the container, and allowing it to drain. The functionalized polyisobutylene compound would be present in the container and the additional polyisobutylene would be immersed in the container. The coated substrate can then be dried, such as by force-drying or baking. Variables, such as immersion speed, dwell time, withdrawal speed, and drying time, can be adjusted based on the desired properties of the product, as generally known to those skilled in the art.

Figure 4:
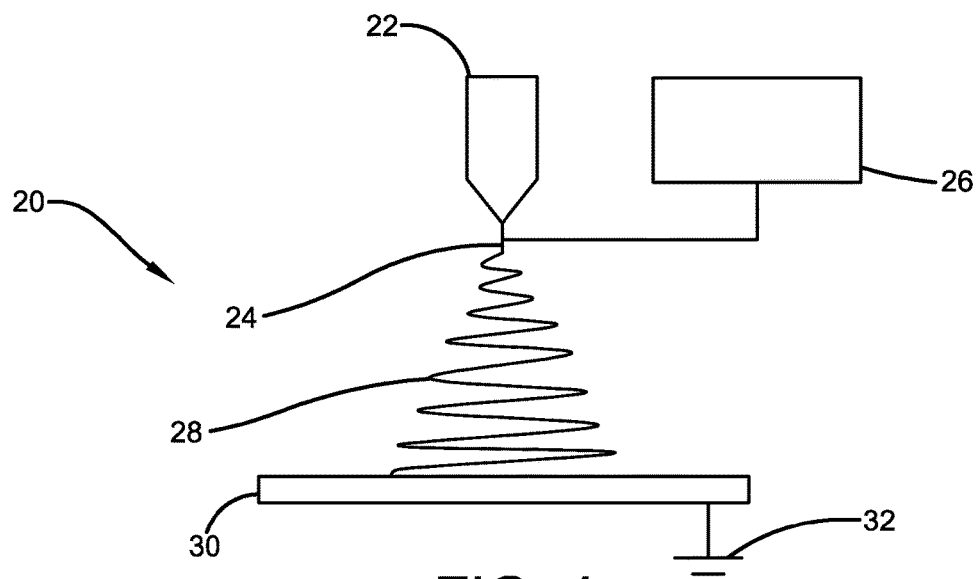
FIG. 4 is a schematic representation of an electrospinning apparatus.

A schematic of an electrospinning apparatus 20 is shown in FIG. 4. In general, electrospinning is a fiber production method which uses electric force to draw charged threads of polymer solutions or polymer melts.

With reference to FIG. 4, functionalized polyisobutylene compound and additional polyisobutylene are pre-mixed in a polymer solution in a collection device 22, such as a syringe. Collection device 22 is includes a needle 24 which is attached to a power source 26 for providing an electric force to the polymer solution. When a sufficient voltage is applied to a liquid droplet, the droplet is stretched, and at a critical point, a stream of liquid, or jet, erupts from the surface. This point of eruption is known as the Taylor cone, generally represented by numeral 28. The jet is then elongated by a whipping process caused by electrostatic repulsion initiated at small bends in the fiber, until it is finally deposited on the collector 30, which is coupled to a ground 32. Variables related to the solution properties, needle variety, and collector type can be adjusted based on the desired properties of the resulting fiber, as generally known to those skilled in the art.

One or more aspects of an electrospinning process may be disclosed in U.S. Pat. Nos. 6,753,454; 8,632,721; and 9,034,240, which are incorporated herein by reference.

In general, electrospraying is related to electrospinning, except that the charged droplet does not form a fiber. Rather, a cloud of tiny, highly charged droplets is formed. As in electrospinning, an electric charge causes the formation of a fine jet. However, in electrospraying, this jet becomes unstable and breaks up into the cloud of fine droplets. Since these droplets are all highly charged with the same electrical charge they repel each other very strongly. Thus, the droplets separate from each other and are able to cover a wide surface area.

One or more aspects of an electrospraying process may be disclosed in U.S. Pat. Nos. 7,951,428 and 8,088,324, which are incorporated herein by reference.

EXAMPLES

Example 1

Thymine-functionalized polyisobutylene (PIB-T) was utilized as an exemplary compound to demonstrate the segregation of the T groups to the surface. Thymine was chosen because of its ability to hydrogen bond, which permits for the attachment of drugs or other molecules to the surface of the polymer as previously done with thymine-functionalized polystyrene (PS-T). It was expected that thymine groups would migrate closer to the surface due to chain mobility. Earlier reports showed that polar groups in non-polar rubbers, with $T_g$ below room temperature, can migrate to the surface in a polar environment due to chain mobility.

PIB-T, was spin-coated onto a layer of arbPIB(OH)-MS (3.5) TPE, which was spin-coated onto a silicon wafer, where the parenthetical number represents the weight percent of methylstyrene (MS) in the TPE. The (OH) represents —OH groups on the PIB core. The PIB block of the PIB-T became entangled into the surface PIB layer of the arbPIB(OH)-MS(3.5).

Film thickness measurements were obtained by ellipsometry for arbPIB(OH)-MS(3.5), PIB-T, and arbPIB(OH)-MS(3.5)/PIB-T, which are given below in Table 1. The results from ellipsometry showed that the blended film, arbPIB(OH)-MS(3.5)/PIB-T was thicker than the arbPIB(OH)-MS(3.5) film. This is an indication that a layer of PIB-T was successfully added to arbPIB(OH)-MS(3.5). When only PIB-T was coated onto the silicon wafer, a thinner layer was obtained than with arbPIB(OH)-MS(3.5) because of the higher molecular weight (higher viscosity) of the latter. Evidence of surface modification was obtained using contact angle measurement to determine if the hydrophilicity of the surface increased with PIB-T.

TABLE 1

Film Thickness of Spin Coated Films

| | arbPIB(OH)-MS(3.5) | PIB-T | arbPIB(OH)-MS(3.5) + PIB-T |
|---|---|---|---|
| Film thickness (nm) | 190.9 nm | 118.2 nm | 228.7 nm |

Contact angle measurements were taken for these samples. The water contact angle of certain samples was taken again after soaking the samples in water for 24 hrs. Contact angle results are shown below in Table 2.

TABLE 2

Water Contact Angle and Hysteresis of surfaces in Example 1.

| | Water Contact Angle | | | |
|---|---|---|---|---|
| Material | Static | Advancing | Receding | Hysteresis |
| TPE (unmodified; arbPIB(OH)-MS)) | 96.7 ± 3.5 | 85.1 ± 7.0 | 74.1 ± 8.3 | 11.0 |
| After soaking in H$_2$O 24 hrs. | 92.8 ± 1.7 | | | |
| PIB-thymine | 81.4 ± 2.3 | 85.1 ± 2.6 | 74.7 ± 3.8 | 10.4 |
| TPE modified by PIB-thymine | 80.2 ± 1.7 | 87.3 ± 1.3 | 73.4 ± 0.9 | 13.9 |
| After soaking in H$_2$O 24 hrs. | 77.9 ± 1.3 | | | |

These results showed that the modified polymer surface increased in hydrophilicity compared to the unmodified TPE, even though the TPE itself contains hydroxyl units. Soaking of arbPIB(OH)-MS(3.5) and PIB-T films in de-ionized water for 24 hours prior to taking contact angles showed a further decrease in the contact angle of arbPIB(OH)-MS(3.5) by approximately 4° and of the PIB-T-modified surface by approximately 2.7°. This was a strong indication that upon exposure to or submersion in aqueous environments, hydrophilic groups reorient to the surface of the material, which results in a decrease in contact angle (i.e. increase in hydrophilicity).

WCA hysteresis has been related to factors such as surface reconstruction of the polymer after liquid contact, and chemical heterogeneity of the top layer (34 in LL paper). The higher standard deviation on the TPE surface indicates more surface roughness.

XPS was carried out to analyze the chemical composition of the surface. Three different grazing angles were used to penetrate the surface of the films to different depths: 15° (approximately 2.5 nm), 45° (approximately 5 nm), and 90° (approximately 10 nm). Table 3 compares the XPS results from arbPIB(OH)-MS and the thymine-modified TPE, arb-PIB(OH)-MS(3.5)/PIB-T. XPS results are shown for two samples at 93.9 eV (low resolution) at 15°, 45°, and 90° angles. When silicon (from silicon dioxide) was found in the samples, the oxygen 1 peaks can be de-convoluted to determine the amount of oxygen from silicon in the samples. When there was silicon present, two bands were seen in the oxygen peak, one at 532 eV from oxygen bound to carbon, and another peak at 534 eV from oxygen in silicone. Using the percentages of each of these peaks gave a better estimation of how much oxygen in the sample was from the silicon. Table 3 shows the XPS results of the fresh polymer samples at 15°, 45°, and 90°, subtracting silicon.

Table 3 also shows that low resolution XPS for arbPIB (OH)-MS showed no detectable nitrogen present at any of the x-ray angles. Oxygen in this sample was only observed at the 45° and 90° X-ray angles.

TABLE 3

XPS results for PIB-based TPE and PIB-based TPE modified with PIB-T

| Sample ID | 15° (Atom %) | | 45° (Atom %) | | 90° (Atom %) | |
|---|---|---|---|---|---|---|
| | N | O | N | O | N | O |
| arbPIB(OH)-MS | ND | ND | ND | 0.4 | ND | 0.3 |
| PIB-T | 0.2 | 1.32 | 0.2 | 6.4 | 0.3 | 2.8 |
| arbPIB(OH)-MS + PIB-T | 0.1 | 0.3 | 0.1 | 0.5 | 0.3 | 0.44 |

Example 2

PIB-OH was used in the modular surface modification of arbPIB-MS. The functionalized PIB-OH was synthesized by hydroboration oxidation and by propylene oxide initiation. Although this example used Cl-PIB-OH, any iteration of PIB-OH is suitable to this example, for example, allyl-PIB-OH and HO-PIB-OH.

The Cl-PIB-OH was then used in the surface modification of arbPIB-MS. To layer, and combine, the functionalized PIB with arbPIB-MS, the functionalized PIB was solubilized and spin coated in a thin layer onto the surface of arbPIB-MS. The surface of the resulting polymer was then characterized. The water contact angle was 80° and the Fg protein adsorption was 298 ng/cm$^2$, which was higher than the TPE alone. Surface characterization data is shown in Table 4. While the WCA was reduced, Fg adsorption was higher on the PIB-OH modified arbPIB-MS than on the non-modified surface.

TABLE 4

Surface characterization data for arbPIB-MS and PIB-OH-modified arbPIB-MS.

| Surface Property | arbPIB-MS | arbPIB-MS + PIB-OH |
|---|---|---|
| Water Contact Angle (°) | 89 | 80 |
| Fg Adsorption (ng/cm$^2$) | 256 | 298 |

Example 3

PIB-HEG was used in the modular surface modification of arbPIB-MS. First the functionalized PIB-HEG was synthesized using PIB-OH with properties of: $M_n$=14,790 g/mol, $M_w/M_n$=1.18. The reactor was loaded with Candida antarctica lipase B (CALB) supported on an acrylic resin (0.035 g resin @ 20 wt % enzyme, $2.10 \times 10^{-7}$ mol, $2.072 \times 10^{-4}$ mol/L) and vacuumed and purged with nitrogen 3 times. Cl-PIB-DVA ($M_n$=14,790 g/mol, $M_w/M_n$=1.18) was reacted with HEG in the presence of CALB to yield PIB-HEG. Cl-PIB-DVA (0.0767 g, $5.30 \times 10^{-6}$ mol, $5.23 \times 10^{-3}$ mol/L) with a chlorine end group and HEG (0.0164 g, $5.80 \times 10^{-5}$ mol, 0.057 mol/L) was dissolved in 3 mL THF. The PIB-DVA/HEG/THF were added to the reactor under $N_2$ atmosphere and then reacted in the presence of CALB for 18 hours. Upon completion, the enzyme was removed by filtration followed by precipitation of the HEG excess in hexane at room temperature. The polymer (PIB-HEG) was then precipitated in cold methanol (5° C.) and dried under vacuum. The yield of this reaction was 0.6253 g and 81.52% conversion. The proton NMR of the product was obtained.

The PIB-HEG was then utilized in the modular surface modification of arbPIB-MS. The surface properties were characterized using water contact angle and SPR for protein adsorption, with results shown in Table 5. As seen, HEG increased Fg adsorption

TABLE 5

Surface characterization data for PIB-HEG modified arbPIB-MS.

| Surface Property | arbPIB-MS | arbPIB-MS + PIB-HEG |
|---|---|---|
| Water Contact Angle (°) | 89 | 79 |
| Fg Adsorption (ng/cm$^2$) | 256 | 334 |

Example 4

PIB-PEG-OCH$_3$ was used in the modular surface modification of arbPIB-MS. First the functionalized PIB-PEG-OCH$_3$ was synthesized. PIB-DVA was reacted with PEG in the presence of CALB to yield PIB-PEG. The solvent used in these syntheses was THF because of the insolubility of PEG in hexane. For these syntheses two different PEGs were used, one where the PEG had a methoxy end group and the second one where the PEG had —OH end group. Cl-PIB-DVA (from SEC: $M_n$=14,790 g/mol, $M_w/M_n$=1.18, 0.4107 g, $2.89 \times 10^{-5}$ mol, 0.009 g/mol) was dissolved in THF, PEG-OCH$_3$ ($M_n$=900 g/mol, $M_w/M_n$=1.12, 0.1974 g, $2.19 \times 10^{-4}$ mol, 0.073 g/mol) was weighed and dissolved in THF as well. CALB (0.114 g resin @ 20 wt % enzyme, $6.84 \times 10^{-7}$ mol, $2.28 \times 10^{-4}$ mol/L) was added to the reactor, which was sealed and purged with vacuum and $N_2$. The dissolved Cl-PIB-DVA and PEG-OCH$_3$ were added to the reactor under $N_2$. The transesterification reaction between the vinyl ester group of Cl-PIB-DVA and the primary hydroxy head group of PEG-OCH$_3$ was carried out under N$_2$ atmosphere at 50° C. under continuous stirring. After 18 hours of reaction time CALB was removed by filtration and the excess PEG-OCH$_3$ was precipitated in hexane. The product PIB-PEG-OCH$_3$ was then precipitated in cold (5° C.) MeOH to remove any impurities and then dried under vacuum. The yield of this reaction was 0.3321 g and 80.86% conversion. A synthetic route was used to yield PIB-PEG-OCH$_3$. The proton NMR of the resulting polymer product was obtained. The PIB-PEG-OCH$_3$ was then used to modify the surface of arbPIB-MS. The modified surface was then characterized, with the results provided in Table 6. As shown, the WCA increased by 9° relative to PIB-HEG in Example 3, Fg adsorption dropped over 80%.

TABLE 6

Surface characterization data for arbPIB-MS and PIB-PEG-OCH$_3$-modified arbPIB-MS.

| Surface Property | arbPIB-MS | arbPIB-MS + PIB-PEG-OCH$_3$ |
|---|---|---|
| Water Contact Angle (°) | 89 | 88 |
| Fg Adsorption (ng/cm$^2$) | 256 | 40 |

XPS studies of the modified film were performed at different angles: 20°, 30°, 45° and 75°. The results in Table 7 show that there was slight oxygen concentration gradient with the highest concentration at the surface of the polymer film. By comparison the unmodified arbPIB-MS only showed 1.8% oxygen when analyzed by XPS at 45°.

TABLE 7

Oxygen detected at different angles by XPS for TPE modified with PIB-PEG-OCH$_3$.

| XPS | % O |
|---|---|
| At 20° (penetration depth ≈ 2.0 nm) | 15.80 |
| At 30° (penetration depth ≈ 5.0 nm) | 15.55 |
| At 45° (penetration depth ≈ 7.1 nm) | 14.41 |
| At 75° (penetration depth ≈ 9.7 nm) | 13.13 |

Example 5

PIB-PEG-OH was used in the modular surface modification of arbPIB-MS. First the functionalized PIB-PEG-OH was synthesized. Allyl-PIB-DVA (M$_n$=10,900 g/mol and M$_w$/M$_n$=1.12, 0.7114 g, 6.52×10$^{-5}$ mol, 0.008 g/mol) was dissolved in THF, PEG-OH (M$_n$=1,100 g/mol, M$_w$/M$_n$=1.10, 0.3500 g, 3.18×10$^{-4}$ mol, 0.039 mol/L) was weighed and dissolved in THF as well. CALB (0.27 g resin @ 20 wt % enzyme, 1.62×10$^{-6}$ mol, 2.02×10$^{-4}$ mol/L) was added to the reactor, which was sealed and purged with vacuum and N$_2$. The dissolved allyl-PIB-DVA and PEG-OH were added to the reactor under N$_2$. The transesterification reaction between the vinyl ester group of allyl-PIB-DVA and the primary hydroxy head group of PEG-OH was carried out under N$_2$ atmosphere at 50° C. under continuous stirring. After 18 hours of reaction time CALB was removed by filtration and the excess PEG-OH was precipitated in hexane. The product allyl-PIB-PEG-OH was then precipitated in cold (5° C.) MeOH to remove any impurities and then dried under vacuum. The yield of this reaction was 0.5855 g and 82.30% conversion. A synthetic route was used to get PIB-PEG-OH. The proton NMR of the resulting polymer product was obtained.

The PIB-PEG-OH was used to modify the surface of arbPIB-MS. The modified surface was then characterized. The water contact angle was found to be 87° and the protein adsorption was 22 ng/cm$^2$. In this case, the WCA was close to that of the PIB-OH modified surface, but Fg adsorption dropped even further.

TABLE 8

Surface characterization data for arbPIB-MS and PIB-PEG-OH-modified arbPIB-MS.

| Surface Property | arbPIB-MS | arbPIB-MS + PIB-PEG-OH |
|---|---|---|
| Water Contact Angle (°) | 89 | 80 |
| Fg Adsorption (ng/cm$^2$) | 256 | 22 |

Further analyses were made on TPE modified with PIB-PEG-OH to determine if the oxygen atoms were closer to the surface of the film. XPS studies of the surface modified film were performed at different angles: 20°, 30°, 45° and 75° and Table 9 gives the results. The results show that there is an oxygen concentration gradient with the highest concentration at the surface of the polymer film. The gradient was much steeper than in the arbPIB-MS+PIB-PEG-OCH$_3$ film.

TABLE 9

Oxygen detected at different angles by XPS for TPE modified with PIB-PEG-OH.

| XPS | % O |
|---|---|
| At 20° (penetration depth ≈ 2.0 nm) | 21.52 |
| At 30° (penetration depth ≈ 5.0 nm) | 21.26 |
| At 45° (penetration depth ≈ 7.1 nm) | 17.63 |
| At 75° (penetration depth ≈ 9.7 nm) | 14.24 |

Example 6

In this example PIB functionalized with the anti-fouling, anti-thrombotic α-lipoic acid was used. The functionalization of PIB with α-lipoic acid (αLA) was not possible through a direct esterification between the PIB with hydroxy group and the αLA. The strategic route followed to achieve this functionalization was first to synthesize TEG-αLA followed by the transesterification between PIB-DVA and the primary hydroxy group of TEG-αLA.

Tetraethylene glycol (TEG, 11.25 g, 0.0579 mol, 5.7921 mol/L) was added to a round bottomed flask. The catalyst, *Candida antarctica* Lipase B (CALB, 0.2025 g, 6.09×10$^{-5}$ mol, 6.09×10$^{-3}$ mol/L), was weighed and added to the reaction flask followed by the addition of α-lipoic acid (αLA, 0.4128 g, 0.002 mol, 0.200 mol/L) The reactor was evacuated and refilled with N$_2$ gas. The reaction was conducted under Nitrogen at 55° C. and continuous stirring. After 4 hours of reaction time the crude product was diluted with THF and filtered to remove the enzyme. The excess THF was removed by rotary evaporation, and the product was redissolved in chloroform.

The product was then washed with acidified water (pH=4.5). MgSO$_4$ was added to the organic phase in order to dry the product. MgSO$_4$ was removed by filtration and the solvent was removed by rotary evaporation. The product was characterized by $^1$H NMR.

PIB-αLA was formed by the transesterification reaction between the primary alcohol of TEG-αLA and the ester group of PIB-DVA. The reaction was carried out under nitrogen and continuous stirring at 50° C. PIB-DVA=10,900 g/mol and $M_w/M_n$=1.12, 0.9121 g, 8.36×10$^{-5}$ mol, 0.0098 mol/L) was weighed and dissolved in 5 mL of THF, TEG-αLA (0.562 g, 0.0014 mol, 0.1721 mol/L) was weighed and dissolved in 3 mL of THF. Ten-fold molar excess of TEG-αLA was used to ensure the complete functionalization of PIB. The catalyst, *Candida antarctica* Lipase B (CALB, 0.2901 g resin @ 20 wt % enzyme, 1.74×10$^{-6}$ mol, 2.04×10$^{-4}$ mol/L), was weighed and added to the reaction flask. The reactor flask was purged with nitrogen. The dissolved PIB-DVA and TEG-αLA were then added to the reactor that contained the enzymatic catalyst. After 24 hrs of reaction time the crude was filtered to remove the enzyme followed by precipitation in cold methanol (5° C.). The product was dried under vacuum and characterized by $^1$H NMR. (Yield: 0.5043 g Conversion: 55.2%). The proton NMR of the resulting functionalized polymer was obtained.

The resulting αLA functionalized PIB compound was then used to surface functionalize arbPIB-MS. The resulting surface modified polymer was then characterized by water contact angle, SPR, and XPS. The water contact angle was 82°. Total Fg adsorption onto the arbPIB-MS+PIB-αLA surface was 14 ng/cm$^2$. arbPIB-MS+PIB-αLA showed the lowest protein adhesion of all tested functionalized PIBs. Statistically significant levels of sulfur were not detected by XPS, indicating that the atoms in the sulfur ring may have been turned inward.

TABLE 10

Surface characterization data for arbPIB-MS and PIB-αLA-modified arbPIB-MS.

| Surface Property | arbPIB-MS | arbPIB-MS + PIB-αLA |
|---|---|---|
| Water Contact Angle (°) | 89 | 82 |
| Fg Adsorption (ng/cm$^2$) | 256 | 14 |

When PIB-αLA was coated directly onto a gold chip substrate (without a layer of TPE), the protein adsorption was 228 ng/cm$^2$. The result is attributed to sulfur atoms having a very high affinity for gold, and the sulfur atoms of the αLA most likely adsorbing preferentially to the gold rather than migrating to the surface. The utility and efficacy of the modular functionalization approach is further demonstrated by this result as the arbPIB-MS+PIB-αLA showed much lower protein adsorption.

Example 7

In this example, arbPIB-MS was electrospun into a fiber mat. The WCA was measured to be 141°, indicating a close to super-hydrophobic surface. The mat was then coated with PIB-αLA, which resulted in a significant reduction of the Fg adsorption.

Example 8

In this example, a mixture of arbPIB-MS and PIB-αLA was electrospun into a fiber mat. The Fg adsorption was also significantly reduced on this fiber mat.

Example 9

Two arbPIB-MS samples were prepared: TPE-1 ($M_n$=210,000 g/mol; $M_w/M_n$=1.7; 3.5 wt % para-methylstyrene PMS), and TPE-2 ($M_n$=202,200 g/mol; $M_w/M_n$=2.80; 13 wt % PMS).

TABLE 11

Fg adsorption on functionalized PIB films on gold chips.

| PIB-ω | Thickness (nm) | Fg Adsorption (ng/cm$^2$) |
|---|---|---|
| PIB-OH | 24 | 375 |
| PIB-HEG-OH | 25 | 334 |
| PIB-PEG-OCH$_3$ | 24 | 70 |
| PIB-PEG-OH | 24 | 62 |

TABLE 12

Fg adsorption on TPE-2 and modular surfaces.

| Coating | Thickness (nm) | Fg Adsorption (ng/cm$^2$) |
|---|---|---|
| TPE-2 | 18 | 256.2 ± 2.1 |
| TPE-2 + PIB-OH | 18 + 7 = 25 | 298.3 ± 20.3 |
| TPE-2 + PIB-PEG-OCH$_3$ | 18 + 7 = 25 | 40.2 ± 4.9 |
| TPE-2 + PIB-PEG-OH | 18 + 7 = 25 | 22.4 ± 1.4 |

TABLE 13

AR XPS results for TPE-2 + PIB-PEG-OCH$_3$ and arbPIB-MS + PIB-PEG-OH surfaces.

| | Atomic O % | |
|---|---|---|
| Grazing Angle | TPE-2 + PIB-PEG-OCH$_3$ | TPE-2 + PIB-PEG-OH |
| 20° | 8.56 | 12.8 |
| 30° | 8.42 | 12.1 |
| 45° | 7.80 | 10.4 |
| 75° | 7.11 | 8.1 |

TABLE 14

Comparison of arbPIB-MS and PIB-α-LA surface properties.

| Coating | Thickness (nm) | Fg Adsorption (ng/cm$^2$) |
|---|---|---|
| TPE-2 | 18 | 256.2 ± 2.1 |
| PIB-α-LA | 26 | 228.0 ± 8.2 |
| TPE-2 + PIB-α-LA | 18 + 7 = 25 | 13.7 ± 0.6 |

TABLE 15

Dynamic WCA and Fg adsorption measured on modular surfaces.

| | WCA(°) | | | Fg Adsorption (ng/cm$^2$) |
|---|---|---|---|---|
| TPE-2 + PIB-ω | Advancing | Receding Start | t = 30 s | |
| PIB-PEG-OCH$_3$ | 112.4 ± 1.5 | 43.1 ± 1.5 | 31.2 ± 1.5 | 40.2 ± 4.9 |
| PIB-PEG-OH | 115.1 ± 2.0 | 42.5 ± 2.0 | 26.0 ± 1.5 | 22.4 ± 1.4 |
| PIB-PIB-α-LA | 113.1 ± 1.5 | 43.3 ± 1.8 | 32.7 ± 3.2 | 13.7 ± 0.6 |

Figure 6:
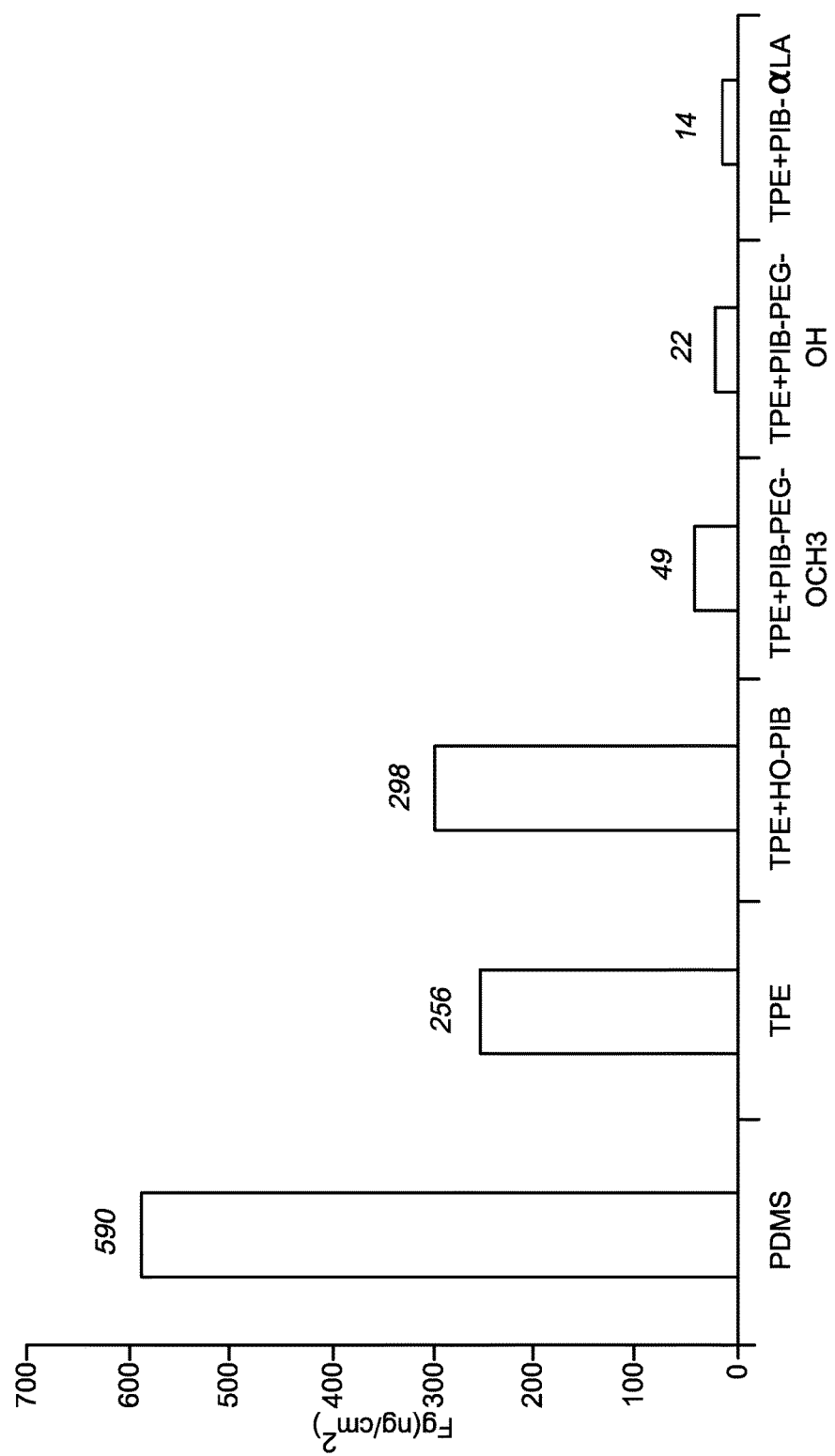
FIG. 6 is a graph showing a comparison of Fg adsorption for various surfaces.

Results:
FIG. 6 shows the comparison of Fg adsorption on various surfaces: PDMS, TPE, and modified TPEs.

Materials:
For the above examples, the following further describes the materials that were utilized.

Propylene epoxide (PE, 99.0%, TCI America) and triethylamine (Et$_3$N, 99.0%, Alfa Aesar) were cryodistilled prior to use. Isobutylene (IB, 99%, ExxonMobil) and methyl chloride (MeCl, 99.9%, Praxair) were condensed from the gas phase after passing them through columns packed with BaO/CaCl$_2$. Hexane (Hx, 98.5%, Mallinckrodt Chemicals) and tetrahydrofuran (THF, 99.9%, Fisher Scientific) were purified with the MBraun MB-SPS purification system. α-Lipoic Acid (α-LA, 98.0%, TCI America) was purified by recrystallization from 75/25 hexanes/heptane. TiCl$_4$ (99.9%, Sigma Aldrich), di-tert-butylpyridine (DtBP, 97%, TCI America), allyltrimethylsilane (ATMS, 97.7%, Gelest Inc.), N,N-Dimethyl acetamide (DMA, 99.8%, TCI America), methanol (MeOH, 99.8%, EMD), sodium bicarbonate (NaHCO$_3$, 99.9%, J. T. Baker), 1,2-ethanedithiol (98%, Fluka), 2-mercaptoethanol (98%, TCI), 2,4,4-trimethyl-1-pentene (TMP-1, 98%, Sigma Aldrich), chloroform (CHCl$_3$, 99.99%, EMD), 2,2-dimethoxy-2-phenylacetophenone (Irgacure® 651, 99.0%, Sigma-Aldrich), divinyl adipate (DVA, 96.0%, TCI America), *Candida antarctica* lipase B (20 wt % CALB immobilized on an acrylic resin, Novozyme® 435 Sigma-Aldrich), Human plasma fibrinogen (Fg, Sigma Aldrich), tetraethylene glycol (TEG, TCI USA), 2,4,4-trimethyl-1-pentanol (98.0%, Acros Organics), 9-borabicyclo[3.3.1]nonane solution (9BBN, 0.5 M in THF, Sigma Aldrich), anhydrous magnesium sulfate (MgSO$_4$, 99.8%, J. T. Baker), potassium hydroxide (KOH, 85.0%, Sigma Aldrich), potassium carbonate (K$_2$CO$_3$, 99.0%, Fischer Chemicals), 30 wt % hydrogen peroxide (H$_2$O$_2$, 30%, Sigma Aldrich), sodium hydride (NaH, 95.0%, Sigma Aldrich), 1-bromo-4-vinyl benzene (98.0%, Sigma Aldrich), acryloyl chloride (97%, Sigma Aldrich), d-chloroform (d-CDCL$_3$, 99.8%, Cambridge Isotope Labs), d-dimethyl sulfoxide (d-DMSO, 99.9%, Cambridge Isotope Labs), dimethyl sulfoxide anhydrous (DMSO, 99.9%, Sigma Aldrich), ethyl ether anhydrous (99.0%, EMD), hexaethylene glycol (HEG, 96.0%, Alfa Aesar), iodomethane or methyl iodide (MeI, 99.0%, Sigma Aldrich), pentane (98.0%, Acros Organics), sodium chloride (NaCl, 99.0%, EMD), sulfuric acid (H$_2$SO$_4$, 96.3%, J. T. Baker), sodium hydroxide (NaOH, 99.5%, Fischer Scientific), poly(ethylene glycol) (PEG, $M_n$=1,100 g/mol, $M_w/M_n$=1.10, Polymer Source), poly(ethylene glycol) monomethyl ether (PEG-OCH$_3$, =900 g/mol, $M_w/M_n$=1.12, Polymer Source), thymine (T, 98.0%, TCI America), 2,4,4-trimethyl-1-pentene (TMP-1, 99.0%, Sigma Aldrich), toluene (99.5%, Mallinckrodt Chemicals), ultra pure water, (H$_2$O, spectroscopic grade, Alfa Aesar), hydrofluoric acid (HF, 48%, Alfa Aesar) were used as received. Phosphate-buffered saline (PBS, pH 7.4, 10 mM, 138 mM NaCl, 2.7 mM KCl, Sigma Aldrich) was degassed for 30 minutes before use. Para-methylstyrene (MS, 98.0%, Acros Organics) was purified using a prepacked column to remove tert-butylcatechol (prepacked column for removing tert-butylcatechol SKU:306320, Sigma Aldrich). Magnesium turnings (Mg, 99.9%, Acros Organics) were sonicated for 30 minutes before use.

Instrumentation and Testing:

For the above examples, the following further describes the instrumentation and testing procedures.

$^1$H and $^{13}$C NMR.

Nuclear magnetic resonance (NMR) spectra were collected at room temperature on Mercury 300 MHz and 500 MHz instruments in CDCl$_3$ (~40 mg/mL) using 90° pulse width. The 300 MHz $^1$H NMR spectra were collected using 128 scans, and the 500 MHz spectra were collected using 512 scans, both with 5 seconds relaxation time. $^{13}$C NMR spectra were obtained using the Mercury 125 MHz instrument with 7000 scans, 1 second relaxation time and 90° pulse width Size Exclusion Chromatography (SEC).

SEC measurements were conducted using a system consisting of an HPLC pump (Waters 515 HPLC Pump), a Waters 2487 Dual Absorbance UV Detector (UV), a Wyatt OPTILAB DSP Interferometric Refractometer (RI), a Wyatt DAWN EOS multi-angle light scattering detector (LS), a Wyatt ViscoStar viscometer (VIS), a Wyatt QELS quasi-elastic light scattering instrument (QELS), a Waters 717 plus autosampler and 6 Styragel® columns (HR6, HR5, HR4, HR3, HR1 and H0.5). The columns were thermostated at 35° C. and THF, continuously distilled from CaH$_2$, was used as the mobile phase at a flow rate of 1 mL/min. The results were analyzed by using the ASTRA software (Wyatt Technology). The molecular weight calculations were carried out using 0.108 mL/g as the do/dc value of polyisobutylene (PIB). The UV spectrometer was set to 240 nm wavelength.

Tensile Testing.

arbPIB-MS was compression molded using laboratory press (Carver Laboratory Press with Omega CN 9000 Temperature Controller), the press was preheated at 170° C. Kapron sheets were used to prevent direct contact of the polymer and the mold with the press. The polymer was preheated on the press and then a force of 3,000 lbs was applied for 8 minutes. The force was increased to 11,250 lbs for 2 minutes. The temperature was decreased to 100° C. and let it sit at the same pressure for 12 more minutes. Then the molded polymer was cooled in liquid Nitrogen and removed from the mold. From the molded sheet of arbPIB-MS microdumbbells were cut following ASTM D412-06 to proceed with tensile testing. The tensile testing was carried out in an Instron 5567 tensile tester with a 1000-N load cell and a cross-head speed of 500 mm/min.

Spin Coating.

Two different substrates were used to spin coat polymer films: silicon wafers and gold chips. Si wafers were blown with N$_2$ gas to remove dust from the surface. In order to remove organic contaminants, the wafers were immersed in a heated piranha solution (H$_2$SO$_4$:30% H$_2$O$_2$ 3:1) for 20 minutes. The silicon wafers were rinsed with deionized water and with purified water. Due to the oxidizing nature of the piranha solution the silicon wafers were hydroxylated (presence of hydroxy groups) making the surface of the Si wafers hydrophilic. The Si wafers were etched with HF:H$_2$O$_2$ solution for 40 seconds and rinsed with deionized water and purified water. After etching the Si wafers with HF solution the surface became hydrophobic. The Si wafers were blown with N$_2$ gas and were ready to use. The gold chips were first rinsed with distilled water followed by a 30 minutes ultrasonic cleaning in detergent solution. Then they were rinsed with distilled water until clean followed by a 30 minutes ultrasonic cleaning in ethanol. The chips were rinsed with ethanol until clean and then soaked in piranha solution for 5 minutes at room temperature. The gold chips were rinsed with distilled water and dried until clean. The chips were exposed to UV/O treatment for 30 minutes. Then they were rinsed with distilled water and dried with air. Solutions of arbPIB-MS, PIB-OH and functionalized PIB were prepared with different concentrations depending on the desired thickness using Toluene as solvent. The substrate was placed on the spin coater die and Toluene filtered with a 0.45 mm PTFE filter was placed on top of the substrate and spun at 2,000 RPMs until a color change was observed. The color change on the chip indicated that the solvent was evaporated. The substrate was covered with the filtered solution of the polymer and it was spun at 2,000 RPMs until a color change was observed.

Protein Adsorption by Surface Plasmon Resonance (SPR).

Protein adsorption of the different PIBs that were synthesized was detected using a four-channel (SPR) sensor. The mentioned sensor measures the differences in wavelength at a light incident angle that is fixed. A fibrinogen solution was prepared in phosphate bovine serum (PBS) with a concentration of 1 mg/mL. The coated gold chip was placed on the prism of the equipment using oil. Once the coated gold chip was placed on the instrument, only buffer (PBS) was passed through the SPR channels for ten minutes establishing a pre-adsorptive baseline. Once the pre-adsorptive baseline was built, the SPR channels were connected to the protein solution that was passed through the SPR channels for ten minutes leaving the proteins on top of the coated gold chip. The proteins that were not attached to the substrate were rinsed from the coated gold chip with buffer (PBS) for 10 minutes establishing a post-adsorptive baseline. A flow rate of 0.05 mL/min was used for all the experiments. Finally, the protein adsorption was quantified by measuring the wavelength shift between the pre-adsorptive and post-adsorptive baselines. The mentioned shift is then converted to the amount of adsorbed protein; 1 nm SPR wavelength shift represents a protein surface coverage of 15 ng/cm$^2$.

Ellipsometry.

Thickness of the spin coated films on the substrates (silicon wafer or gold chip) was measured using a J. A. Woollam Co. variable-angle spectroscopic ellipsometer. Before analyzing the thickness of the films the instrument was calibrated using a standard silicon wafer.

Water Contact Angle.

The contact angle goniometer Rame Hart Inc., Model #100-0-7-00 was used to measure the water contact angle of different polymers. Drops of 5 µL in size of DI water were placed on the polymer-coated substrate.

X-Ray Photoelectron Spectroscopy.

The polymers that were spin coated on gold chips were analyzed by XPS in ultra high vacuum using a PHI VersaProbe II Scanning XPS Microprobe. The samples were analyzed in a range from 0 to 600 eV with a beam diameter of 100 microns and a penetration depth of 10 nm. The X-ray beam was set to 15°, 45° or 90° to analyze the surface of the films at different angles.

In light of the foregoing, it should be appreciated that the present invention advances the art by providing a polymer composite comprising a functionalized polyisobutylene and an additional polyisobutylene-containing material and one or more methods of making the polymer composite. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A polymer composite comprising a functionalized polyisobutylene and an additional polyisobutylene-containing material, wherein the functionalized polyisobutylene includes an α-lipoic acid functional group.

2. The composite of claim 1, wherein the functionalized polyisobutylene and the additional polyisobutylene-containing material are not attached by a covalent bond.

3. The composite of claim 1, wherein the additional polyisobutylene-containing material is non-functionalized.

4. The composite of claim 1, wherein the additional polyisobutylene-containing material is selected from the group consisting of linear polyisobutylene thermoplastic elastomers (TPEs), star polyisobutylene TPEs, and arborescent polyisobutylene TPEs.

5. The composite of claim 1, wherein the additional polyisobutylene-containing material is an arborescent polyisobutylene-based TPE with poly(para-methyl styrene) end blocks (arbPIB-MS).

6. A coated substrate comprising the composite of claim 1, coated on a substrate.

7. The coated substrate of claim 6, wherein the substrate is a breast implant.

8. The coated substrate of claim 6, wherein the composite has a protein adsorption less than 25 ng/cm$^2$ with respect to the protein fibrinogen.

9. The coated substrate of claim 6, wherein the functionalized polyisobutylene forms a functionalized polyisobutylene compound layer having a thickness, wherein the thickness of the functionalized polyisobutylene compound layer is less than 1 micron.

10. The coated substrate of claim 6, wherein the functionalized polyisobutylene forms a functionalized polyisobutylene compound layer having a thickness, wherein the thickness of the functionalized polyisobutylene compound layer is less than 20 nm.

11. The coated substrate of claim 6, the composite having a thickness, wherein the thickness of the composite is less than 1 micron.

12. The coated substrate of claim 6, the composite having a thickness, wherein the thickness of the composite is less than 20 nm.

13. The coated substrate of claim 6, the composite having a surface, wherein a drug or molecule is attached to the surface of the composite.

14. A method for producing the polymer composite of claim 1, comprising steps of providing the additional polyisobutylene-containing material as a substrate having a surface, and coating the surface of the substrate with the functionalized polyisobutylene.

15. The method of claim 14, wherein the step of coating includes spray coating the functionalized polyisobutylene onto the surface of the substrate.

16. The method of claim 14, wherein the step of coating includes dipping the surface of the substrate in a solution containing the functionalized polyisobutylene.

17. A method for producing a coated substrate including the polymer composite of claim 1, comprising steps of
providing a polymer combination comprising the functionalized polyisobutylene and the additional polyisobutylene-containing material, and
depositing the polymer combination on to a substrate to thereby form the coated substrate.

18. The method of claim 17, wherein the step of depositing is electrospraying.

19. The method of claim 17, wherein the step of depositing is electrospinning.

* * * * *